(12) United States Patent  
Harrington (10) Patent No.: US 7,658,192 B2
(45) Date of Patent: Feb. 9, 2010

(54) METHOD AND DEVICE FOR TREATMENT OF OBSTRUCTIVE SLEEP APNEA

(75) Inventor: Douglas C. Harrington, 1145 El Abra Way, San Jose, CA (US) 95125

(73) Assignee: Douglas C. Harrington, San Jose, CA (US)

( * ) Notice: Subject to any disclaimer, the term of this patent is extended or adjusted under 35 U.S.C. 154(b) by 0 days.

(21) Appl. No.: 11/772,910

(22) Filed: Jul. 3, 2007

(65) Prior Publication Data

US 2009/0007922 A1 Jan. 8, 2009

(51) Int. Cl.
*A61F 5/56* (2006.01)
*A61F 13/00* (2006.01)
*A61B 5/117* (2006.01)

(52) U.S. Cl. .................. 128/848; 128/846; 433/229
(58) Field of Classification Search ............... 128/848
See application file for complete search history.

(56) References Cited

U.S. PATENT DOCUMENTS

| | | | | |
|---|---|---|---|---|
| 6,159,208 | A  * | 12/2000 | Hovda et al. | 606/41 |
| 6,390,096 | B1 * | 5/2002 | Conrad et al. | 128/897 |
| 7,360,542 | B2 * | 4/2008 | Nelson et al. | 128/848 |
| 2004/0149290 | A1 * | 8/2004 | Nelson et al. | 128/848 |
| 2008/0066764 | A1 * | 3/2008 | Paraschac et al. | 128/848 |
| 2008/0208265 | A1 * | 8/2008 | Frazier et al. | 606/326 |

* cited by examiner

*Primary Examiner*—Patricia M Bianco
*Assistant Examiner*—Victoria Hicks
(74) *Attorney, Agent, or Firm*—K. David Crockett, Esq.; Niky Economy Syrengelas, Esq.; Crockett & Crockett (57) ABSTRACT

This invention relates to devices and methods for maintaining upper airway patency during sleep for the treatment of sleeping disorders, upper airway resistance syndrome, snoring and obstructive sleep apnea.

13 Claims, 6 Drawing Sheets

Fig. 6

METHOD AND DEVICE FOR TREATMENT OF OBSTRUCTIVE SLEEP APNEA

FIELD OF THE INVENTIONS

The inventions described below relate the field of methods and devices for treatment of sleeping disorders, upper airway resistance syndrome, snoring and obstructive sleep apnea.

BACKGROUND OF THE INVENTIONS

According to a report published in the April 2004 Journal of the American Medical Association, it is estimated that one in five adults, or approximately 44 million people in the United States suffers from mild obstructive sleep apnea (OSA) and that approximately 15 million people in the United States suffer from moderate or more severe OSA. In a separate report, the American Association of Orthodontists estimates that 55 million people in the United States suffer from habitual or socially disruptive snoring.

Obstructive sleep apnea is caused by the closing of the upper airway while a person is asleep. The uvula and soft pallet collapses on the back wall of the upper airway. Then the tongue falls backward, collapsing on the back wall of the upper airway, the uvula and soft pallet forming a tight blockage, preventing any air from entering the lungs. The effort of the diaphragm, the chest and the abdomen only cause the blockage to seal tighter. In order to breathe, the person must arouse or awaken. This creates tension in the tongue thereby opening the airway, allowing air to pass into the lungs.

Obstructive sleep apnea causes a drop in a person's blood oxygen saturation ($SaO_2$) and an increase in the blood's carbon dioxide ($CO_2$). When the $SaO_2$ drops the heart will start pumping more blood with each beat. If the $SaO_2$ continues to drop the heart will start beating faster and faster. As the $CO_2$ increases the brain will try to drive the person to breathe. The effort and action of the abdomen and chest will increase. Eventually that action will clear the upper airway blockage, allowing the person to breathe. A cyclic process of arousal and falling back to sleep will typically occur throughout the person's sleep.

The American Academy of Sleep Medicine rates the average number of OSA events per hour as your Respiratory Distress Index (RDI). An RDI of 0 to 5 is normal; 5 to 20 is mild; 20 to 40 is moderate; over 40 is considered severe. An apnea event must last at least 10 seconds to be considered an event. It is not uncommon to see RDIs well above the 40. In some cases RDIs were well above 100, with events lasting as long as 90 to 120 seconds and $SaO_2$s going below 70% when normal is 95% to 100%.

Obstructive sleep apnea is a serious, potentially life-threatening condition that is far more common than generally understood. Recent studies have linked OSA with increased risks of cardiovascular morbidity, high blood pressure, stroke, heart attack, Type II diabetes and depression. OSA typically causes excessive daytime sleepiness, resulting in memory loss, lack of concentration, slower reaction time that can cause difficulty driving or operating equipment and sexual dysfunction, such as impotence and libido.

There are several methods, devices and surgical procedures presently available for the treatment of OSA. The most frequently prescribed and most common treatment is continuous positive airway pressure, or CPAP. CPAP therapy requires that the patient wear a nasal or facial mask during sleep that is connected by a tube to a portable airflow generator, which delivers air at a predetermined continuous positive pressure. The continuous positive pressure forces air through the nasal passages and opens the back of the throat, keeping the upper airway open and unobstructed during sleep. CPAP prevents upper airway closure while in use, but apnea or hypopnea episodes return when CPAP is stopped or used improperly. CPAP is not a cure for OSA, but a lifelong therapy for managing OSA that must be used on a nightly basis. Noncompliance rates for CPAP are estimated to exceed 50% due to factors such as physical discomfort and claustrophobia resulting from use of the nasal or facial mask, nasal and facial irritation, uncomfortable sleeping positions, lifestyle changes, social factors and inconvenience.

Another mechanical therapy prescribed to treat OSA is a custom fitted or prefabricated orthodontic like device or oral appliance that is worn while sleeping. An oral appliance attempts to reposition the jaw and/or the base of the tongue to prevent the tongue from collapsing and obstructing the upper airway during sleep.

When surgical therapy is indicated, conservative procedures are attempted first. These procedures include uvulectomy, nasal reconstruction, Aden tonsillectomy, uvulopalatopharyngoplasty (UPPP or UP3) and laser assisted uvulopalatoplasty (LAUP). Second line treatments for OSA are more complex and include genioglossal advancement with or without hyoid myotomy, maxillary mandibular advancement, bimaxillary advancement, and tongue base surgery. The more invasive of these surgical procedures are very painful, usually require post procedure prescription narcotics to manage pain, often result in potentially serious post surgical complications which can involve hospital readmission, usually result in lengthy recovery periods and are expensive to administer.

Uvulopalatopharyngoplasty, currently the most common palatal surgical treatment for both OSA and snoring, uses a scalpel, electrocautery, coblation or other cutting technology to remove excess tissue at the back of the throat (tonsils, uvula, and part of the soft palate) under general anesthesia. The UPPP procedure is very painful, often requires an overnight hospital stay, sometimes requires hospital readmission to resolve complications, and typically involves lengthy recovery period of up to two weeks. Surgical success rate is approximately 50% when surgical success is defined as both 50% reduction in RDI and a postoperative RDI of less than 20. This is despite preselection of patients where the uvula and soft palate are identified as the cause of OSA.

Laser assisted uvulopalatoplasty is similar to UPPP, but uses heat from a laser to destroy tissue of the soft palate. The LAUP procedure requires the use of expensive laser capital equipment and often involves multiple treatments. The clinical and economic benefits of using LAUP over UPPP have not been well established and as a result, LAUP procedures are now performed infrequently.

A vast majority of people with OSA have tongue base narrowing or posterior displacement of the tongue into the airway. Several highly invasive surgical procedures with concomitant high morbidity but significantly improved clinical results compared to UPPP and LAUP have been used to address this issue. Genioglossal (primary muscle of the tongue) advancement involves performing a mandibular osteotomy (reconstruction of the lower jaw) with anterior repositioning of the genioglossus attached segment of the mandible, which results in anterior displacement of the tongue. This procedure is painful and requires long recovery and sometimes results in permanent numbness of the lower front teeth.

Maxillomandibular advancement is the most invasive and effective surgical treatment for OSA. The procedure involves moving both the maxilla (upper jaw) and the mandible forward to establish an open airway. Success rates of 90% to 100% with maxillomandibular advancement surgery as the primary procedure have been reported. While speech and swallowing are typically not affected, this procedure is painful, requires a long recovery and sometimes it causes numbness of the lower lip and some changes in facial appearance. Chewing is not allowed for 4 weeks and typically, patients will not return to work in less than one month post procedure.

SUMMARY

The present invention relates to a system and method for restraining a patient's tongue from falling back into the throat when sleeping to prevent sleep related breathing disorders. A portion of the patient's tongue tissue is wounded and a silicone tongue restrainer is inserted into the tongue tissue and secured to the patient tissue or bone. The restrainer is sized and dimensioned to fit within the patient's mouth into the wounded tongue tissue and the restrainer comprises pores that are sized and dimensioned to support growth of vascularized tissue within the restrainer and capable of suspending the tongue away from the patient's throat during sleep.

DETAILED DESCRIPTION OF THE INVENTIONS

Figure 1:
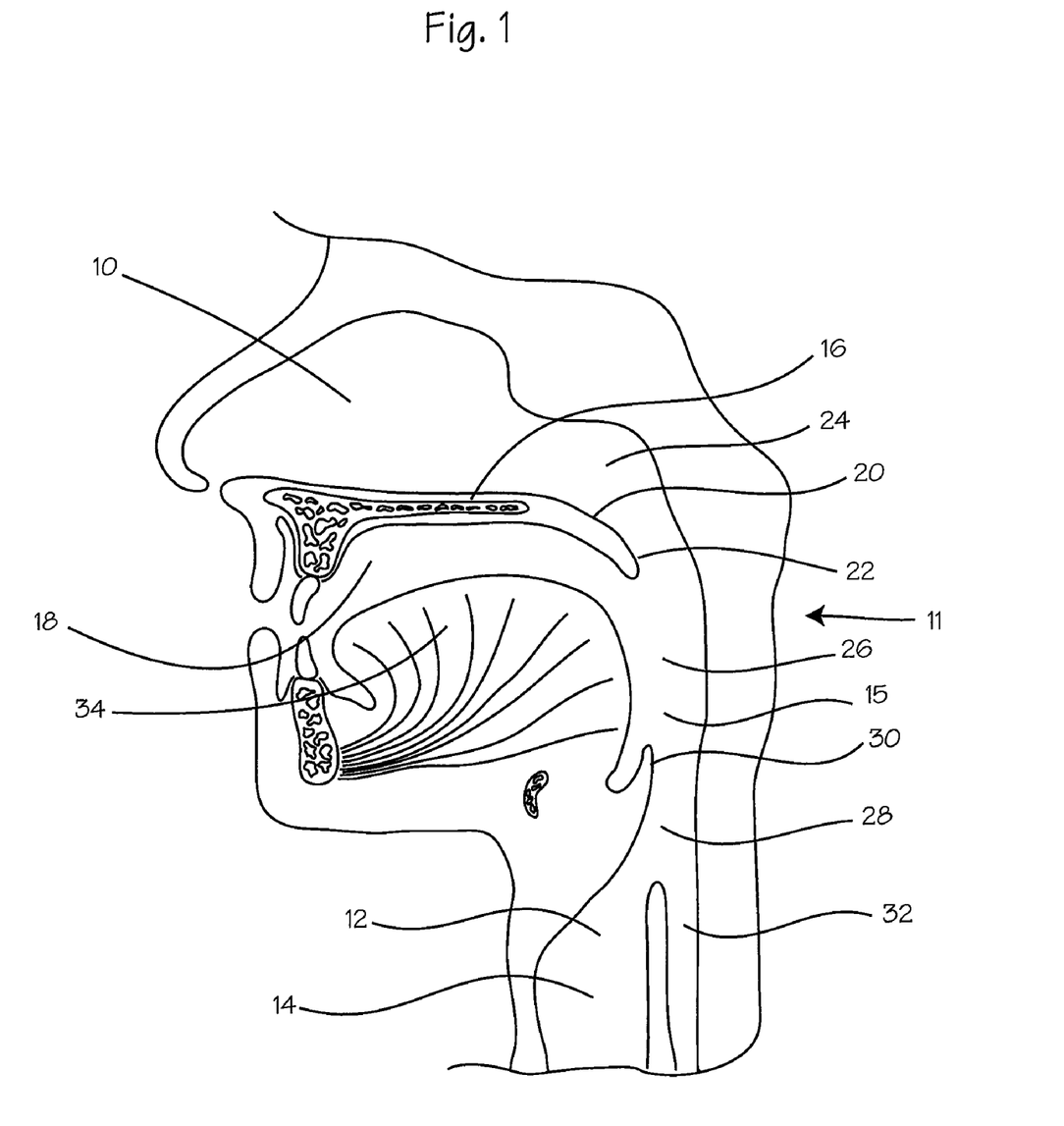
FIG. 1 is a partial sectional view through the head and neck of an individual.

FIG. 1 illustrates the normal anatomy of the human upper respiratory system consisting of the nasal cavity 10, pharynx 11 and larynx 12 which communicates with the trachea 14 (or windpipe). The nasal cavity is located inside the external nose or joins the pharynx. The floor of the nasal cavity is composed of the hard palate 16, a bony plate covered by mucosa that separates the oral cavity 18 from the nasal cavity. Posterior to the hard palate is a non-bony segment of tissue, the soft palate 20, which consists of skeletal muscle and connective tissue. The uvula 22 is a soft process that extends downwardly from the posterior edge of the soft palate.

The pharynx is divided into three regions, the nasopharynx 24, the oropharynx 26, and the laryngopharynx 28. The nasopharynx is the superior portion of the pharynx, which extends from the nasal cavity to the level of the uvula. The oral cavity opens into the oropharynx, which extends from the uvula to the epiglottis 30. The laryngopharynx extends from the tip of the epiglottis to the openings of the larynx and the esophagus 32.

The tongue 34 consists of a mass of intrinsic muscles, which are involved in changing the shape of the tongue, and extrinsic muscles, which help change the shape and move the tongue. The major extrinsic muscles include the hyoglossus, styloglossus, palatoglossus and genioglossus. The genioglossus' primary function is depression and protrusion of the tongue.

Figure 2:
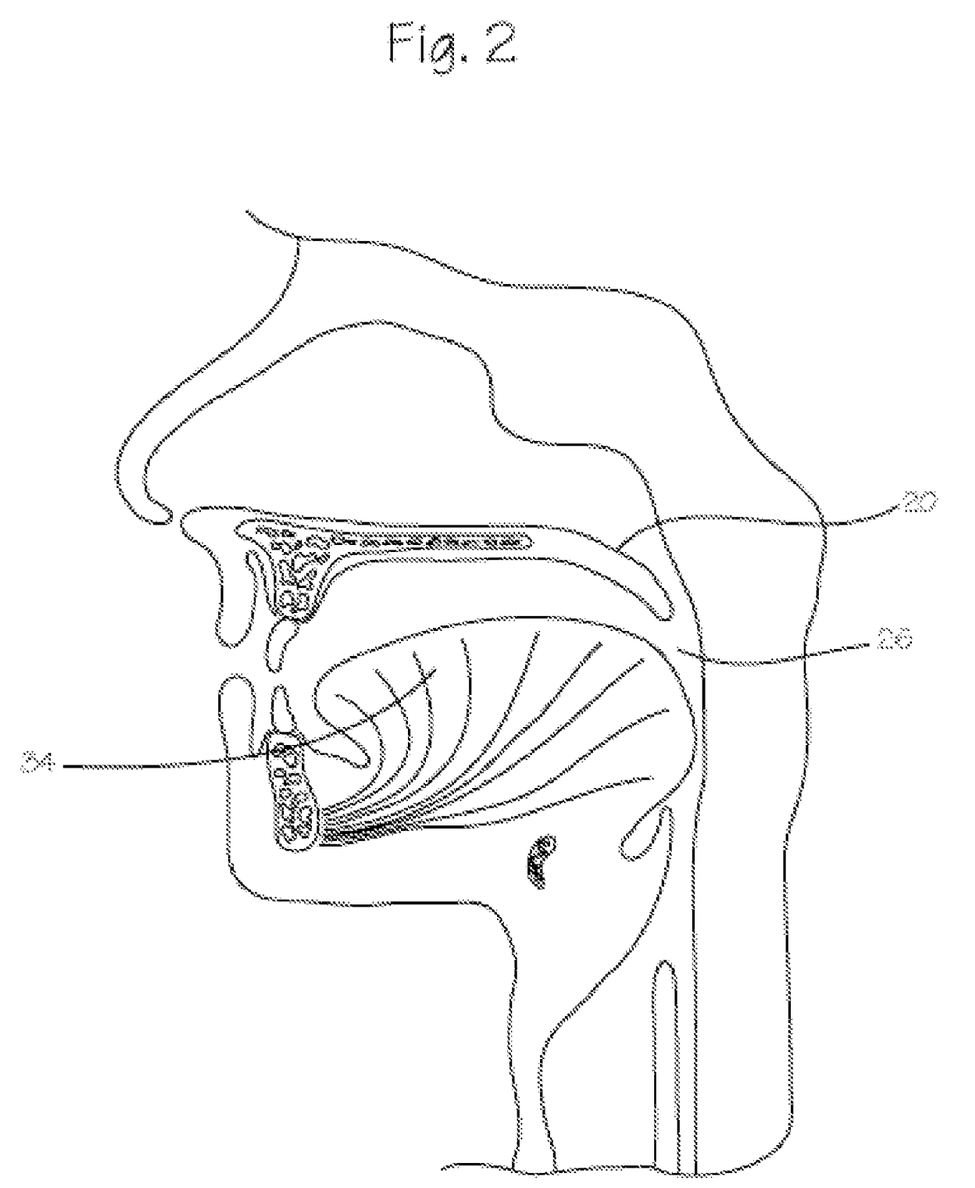
FIG. 2 is a view illustrating occlusion of the oropharynx that occurs during obstructive sleep apnea.

FIG. 2 is a view illustrating occlusion of the oropharynx 26 that occurs during obstructive sleep apnea. Obstructive sleep apnea is caused by repetitive airway obstruction during sleep as a result of narrowing of the respiratory passages. The base of the tongue 34 is the most common site of obstruction in sleep apnea. The obstruction or collapse of the passageway occurs when the base of the tongue abuts the posterior wall and soft palate 20. Decreased airway muscle tone during sleep and the pull of gravity in the supine position can further decrease airway size, further impeding airflow during respiration.

FIGS. 3a through 4d are views of various configurations of tongue restrainers 36 for use in preventing the tongue from collapsing into the throat when sleeping. The device shown in the figures comprises a silicone restrainer that is capable of being positioned into the base of the tongue or posterior portion of the tongue of a patient to restrain or prevent the tongue from collapsing posteriorly or back towards the throat during sleep. The restrainer can be variously shaped and may be a strip, sheet, rod or string of material and is sized and dimensioned to fit within a patient's mouth. The restrainer contains pores that are sized and dimensioned to support growth of vascularized tongue tissue within the pores. The restrainer can be secured into the tongue muscle or placed just below the mucosal tissues.

The restrainer can be attached to adjacent tissues or bones to assist supporting the tongue base or alternatively implanted into the tongue base without further attachment. Attachment of the restrainer to tissues and bone can be accomplished in various ways including use of bone screws, surgical staples, sutures or any other suitable means for anchoring the restrainer in place.

Figures 3A, 3B, 3C, 3D:
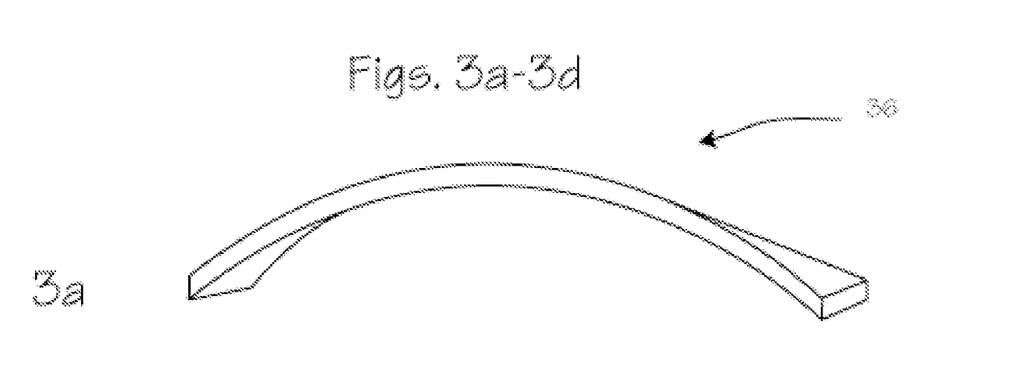
FIGS. 3a through 3d are views of various configurations of planar tongue restrainers for use in preventing the tongue from collapsing.
Figure 3B:
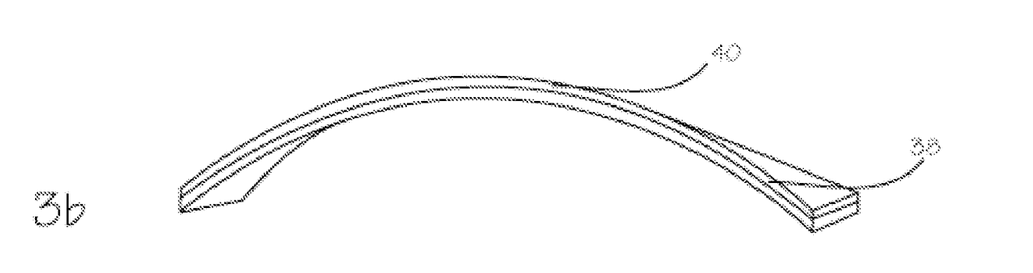
Figure 3C:
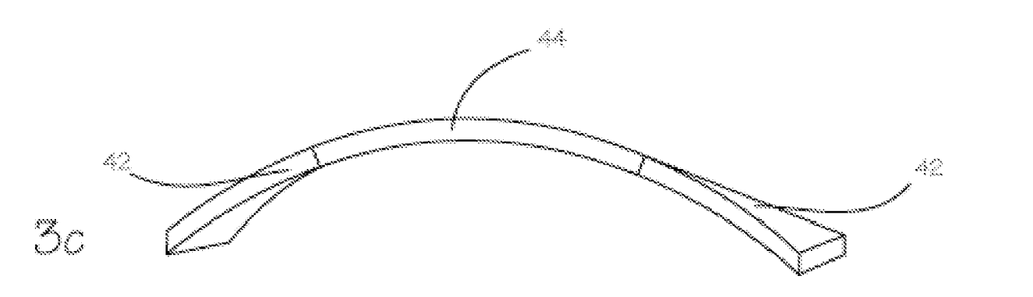
Figure 3D:
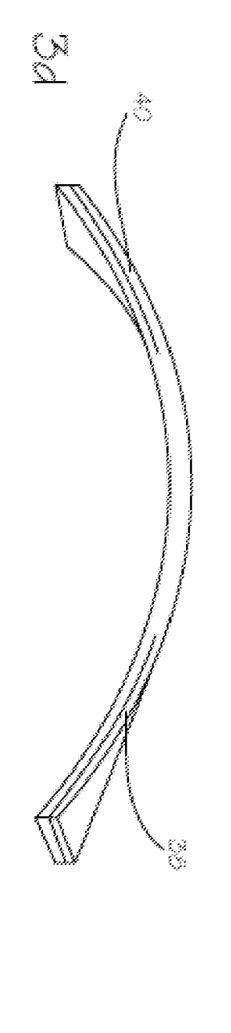

FIGS. 3a through 3d illustrate various planar restrainer configurations. FIG. 3a is a view of a planar restrainer 36 made of silicone. The restrainer can be a sheet that is either solid or porous throughout. FIG. 3b is a view of a planar restrainer consisting of a sheet of silicone with a solid portion 38 sandwiched in between two porous sections 40. FIG. 3c is a view of a planar restrainer consisting of individual sections, two outer sections 42 and an inner section 44. The two outer sections can be made of a different silicone than the inner section allowing for variations of hardness and porosity along the restrainer. FIG. 3d is a view of a planar restrainer that is a combination of the restrainer of FIGS. 3b and 3c. This configuration is a planar sheet of silicone with solid sections of silicone 38 sandwiched in between two outer porous sections 40 located at both ends. Alternatively, the restrainer can be a porous sheet with reinforcing materials such as fibers and meshes located at the ends. The pores contained on the restrainer are sized and dimensioned to support growth of vascularized tongue tissue within the restrainer. The planar restrainers are approximately 2 to 16 centimeters in length, 2 to 30 millimeters in width and 0.5 to 5 millimeters in thickness. One example of a planar restrainer configuration would be approximately 10 centimeters in length, 1 centimeter in width and 2 millimeters in thickness.

Figure 4A:
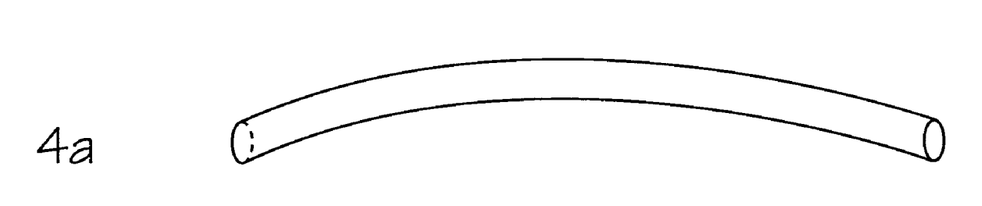
FIGS. 4a through 4d are views of various configurations of cylindrical tongue restrainers for use in preventing the tongue from collapsing.
Figure 4B:
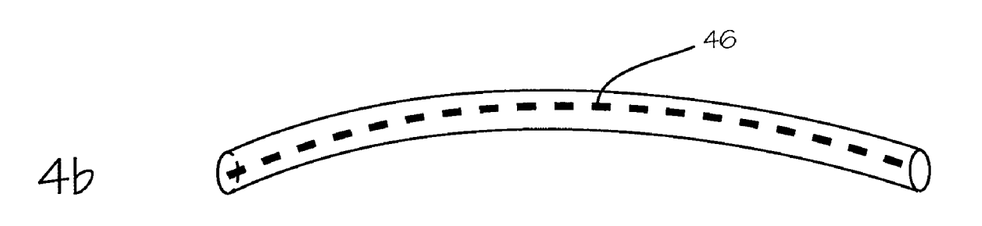
Figure 4C:
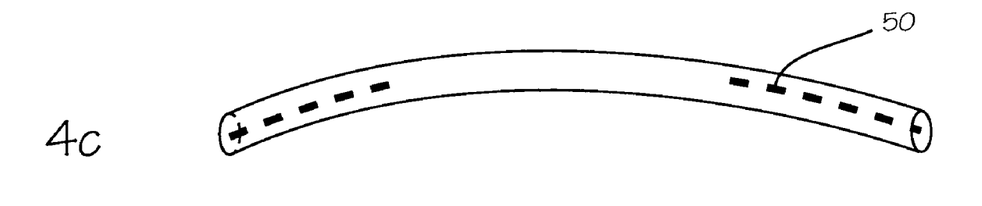
Figure 4D:
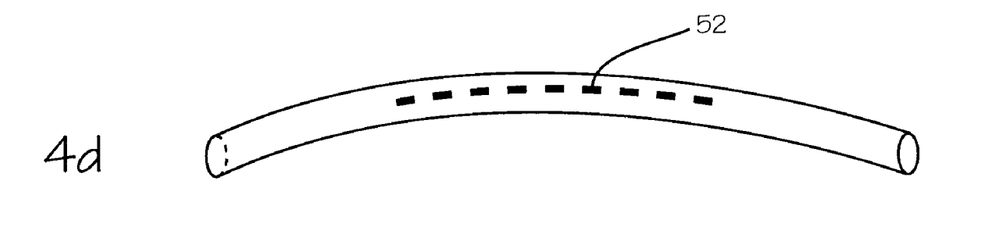

FIGS. 4a through 4b illustrate various cylindrical restrainer configurations. FIG. 4a is a view of a cylindrical restrainer made of silicone. The restrainer can be either solid or porous throughout. FIG. 4b is a view of a cylindrical restrainer consisting of a solid center section 46 throughout the length of the cylinder. The solid section may also contain reinforcing materials such as filaments and fibers. FIG. 4c is a view of a cylindrical restrainer consisting of two solid center end sections 50 to allow for variable properties along the cylindrical restrainer. FIG. 4d is a view of a cylindrical restrainer with a solid central section 52 allowing for variable properties along the cylindrical restrainer. The cylindrical restrainers are approximately 2 to 16 centimeters in length, 1 to 10 millimeters in diameter. One example of a cylindrical restrainer configuration would be approximately 10 centimeters in length and 3 millimeters in diameter.

The restrainers 36 can be made of various types of silicones possessing different properties. For example, the material could be elastic in nature so that during mastication (chewing and swallowing) the tongue is allowed to move posteriorly and in natural motions. In this way, the restrainer would only create enough muscle resistance or support to restrain or prevent the tongue from falling back into the larynx during muscle relaxation that occurs during deep sleep. The restrainer is not used to pull the tongue forward, only to restrain or prevent the tongue from falling back into the throat of the patient when sleeping, particularly when the patient is lying on his back. This elastic characteristic could also prevent erosion or extrusion of the restrainer during repetitive motion that would most likely occur if only simple non-compliant, inelastic surgical suture was employed for this application. Suitable materials with these characteristics include silicone polymers, natural rubbers, thermoplastic elastomers such as thermoplastic polyurethane (Pellethane™, Tecoflex™, Tecothane™ Versaflex™), polyetheramide (Pebax™), styrene block copolymers (Kraton™, Dynaflex™), thermoplastic vulcanizate (Versaflex™) and others. The porous sections of the restrainer can be reticulated, meaning that the pores communicate with other pores, rather than existing as discrete and isolated voids within the material.

The restrainer may also be fabricated from expanded Polytetrafluoroethylene, commonly referred to as ePTFE. The restrainer could also just be covered with ePTFE or placed only on specific sections of the restrainer. One method of manufacturing ePTFE starts with a PTFE rod or sheet, the rod is stretched to expand the PTFE to form the system of nodes and fibrils characteristic of ePTFE.

Where nonporous sections are incorporated into the restrainer, the sections can either be solid material with or without reinforcing members such as polyester or polyethylene or propylene or Kevlar fibers, threads and/or meshes. Incorporation of reinforcing components at the ends of the restrainer assists in attachment to tissues such as the mandible bone by a bone screw and prevents the restrainer from tearing once in place. Placement of reinforcement in the middle and other sections controls the amount of stretch or elasticity desired within the restrainer.

In use, the restrainer can be implanted into the tongue tissues by various methods. To place a restrainer, a surgeon forms a lateral channel at the base of a patient's tongue. The surgeon then places a strap into the lateral channel and secures the ends of the strap to the interior surface of the mandible. The surgeon can also form the lateral channel at the same time that he places the strap into the channel by using a needle passer that pulls the strap implant through the tissue as it simultaneously tunnels through the tissue. This method is similar to the various techniques employed for placement of devices used for the treatment of female urinary stress incontinence. Alternatively, the surgeon can perform tissue incision and dissection with a scalpel or electrosurgical devices. The surgeon can dissect the tissue from a superior approach and tissue pockets or chambers can be created within the tissue. The surgeon may also pre-treat the patient tissue with an energy source such as thermal energy, radiofrequency energy, cryogenic energy and the like to stimulate an inflammatory response to assist with tissue ingrowth into the restrainer.

Figure 5:
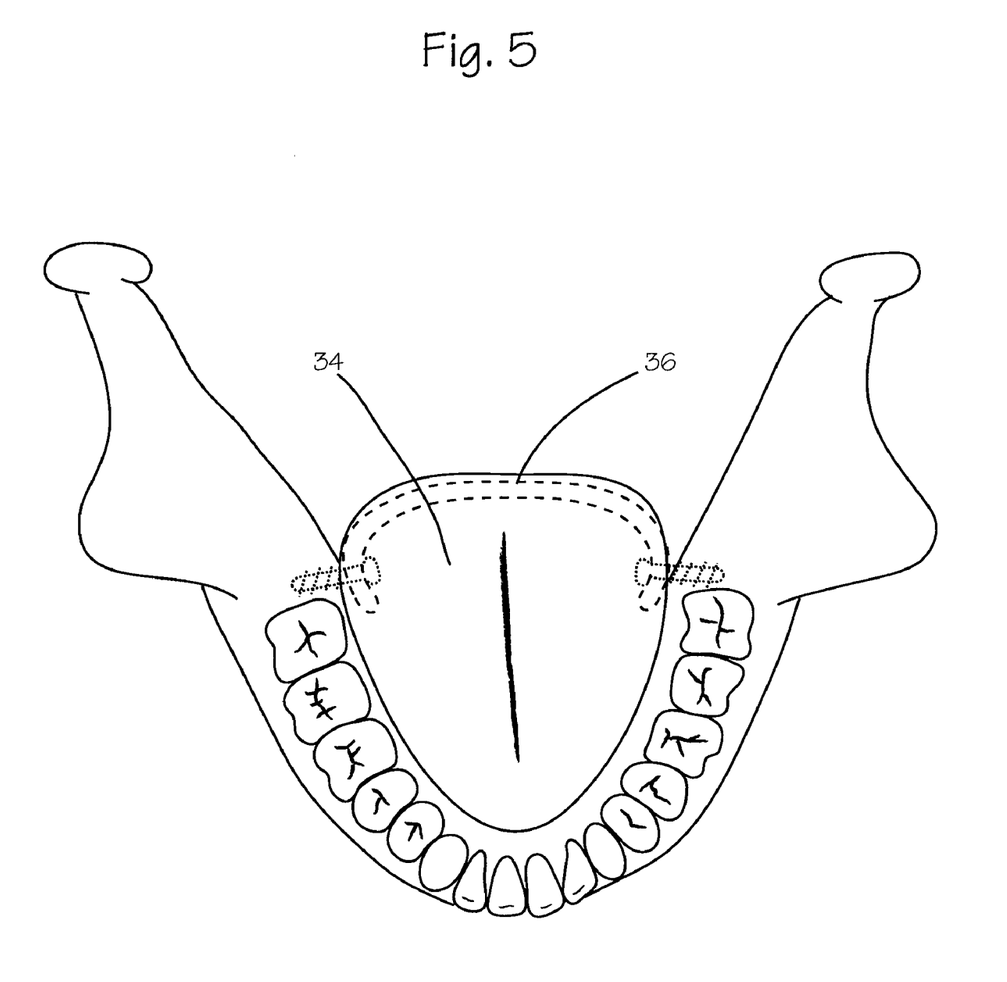
FIG. 5 is a view of the mandible bone with one of the tongue restrainers in place.

FIG. 5 is a view of the mandible bone with one of the tongue restrainers 36 in place. The restrainer is positioned into a channel within the patient's mouth. The restrainer is capable of being positioned into the base of the tongue or posterior portion of the tongue of the patient to prevent the tongue from collapsing posteriorly while the patient is sleeping.

Figure 6:
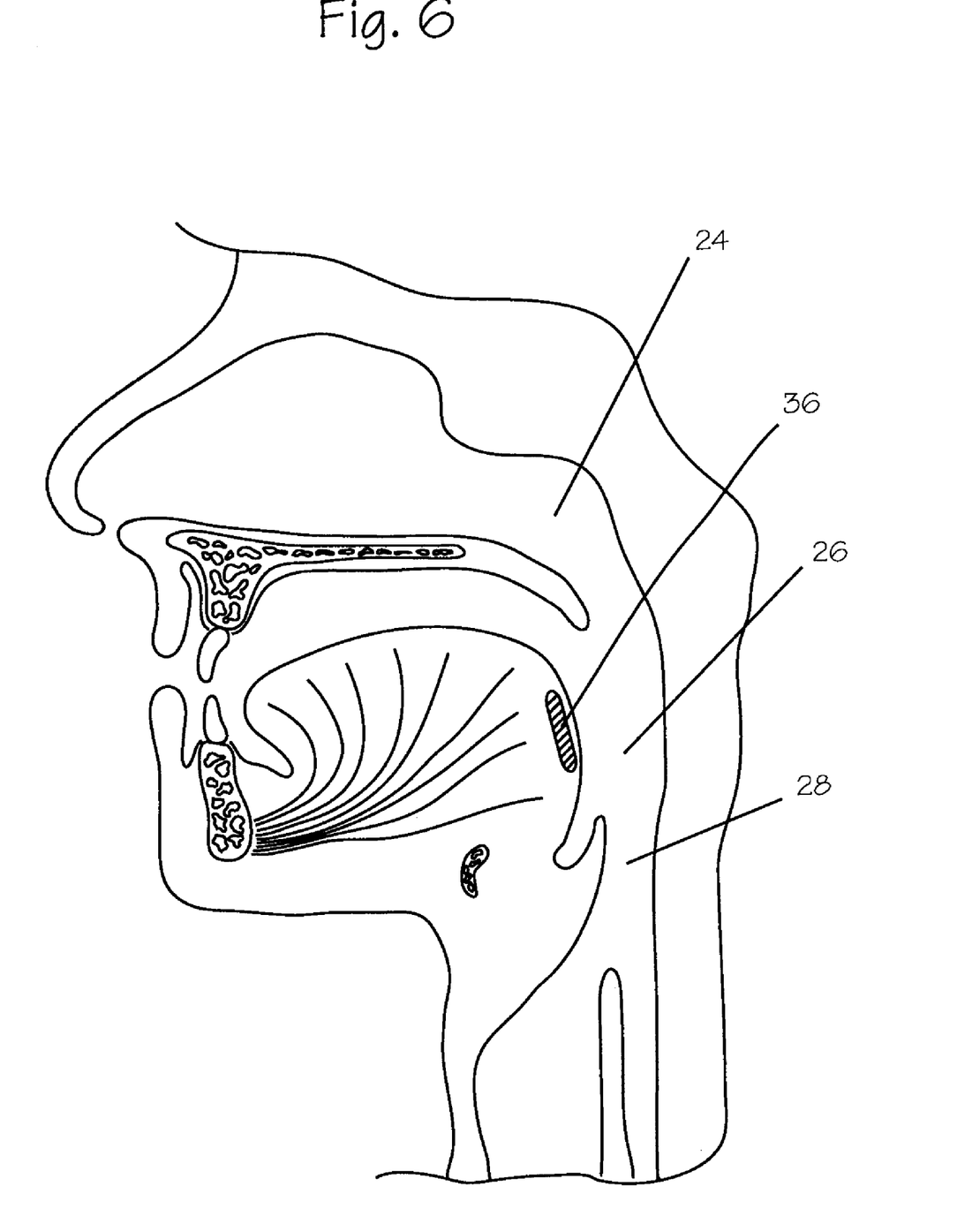
FIG. 6 is a view through the head and neck with a tongue restrainer in place.

FIG. 6 is a view through the head and neck with a tongue restrainer in place. The restrainer is positioned within the lateral channel formed by the surgeon and secured to the inner surface of the mandible. The restrainer is positioned between the nasopharynx 24 and the laryngopharynx 28 within the channel so that the restrainer prevents occlusion of the oropharynx 26.

Placement of a restrainer having suitable flexibility, architecture and pore size into the excised tissue encourages healing tissue to grow into the restrainer. Ingrowth of healthy vascularized tissue into the restrainer prevents or discourages formation of scar tissue around the restrainer and minimizes the potential for restrainer migration and extrusion. Where the pore size is large relative to the cell size, in the range of 40-200 microns, and of a specific architecture, the body will heal by forming a vascularized tissue within the pores of the restrainer. A porous restrainer in its final form will comprise numerous filaments of the foam superstructure, which form a network of communicating pores, with vascular tissue occupying the pores. Large pore size materials can be manufactured in various ways including sintering and molding. For example, porous silicone can be made by injecting polydimethylsiloxane into a form packed with granules. The silicone is cured and the particles are dissolved in a suitable solvent (water, where sugar or salt is used) to form the porous restrainer with communicating pores. Pore size is determined by the size of the dissolved particles. The porous silicone implant can have a durometer value between 20-100 Shore A.

The restrainer can be implanted during one surgical procedure and affixed to the anchor points (e.g. bone) during a second procedure. This would allow tissue to sufficiently grow into the implant before fixation of the implant. A second procedure may be performed from several days to months from the first.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method for maintaining a patient's tongue to prevent sleep related breathing disorders comprising the steps of:
   forming a lateral channel at the base of the patient's tongue;
   positioning a restrainer, said restrainer being elastic, and said restrainer being sized and dimensioned to fit into the lateral channel wherein the restrainer is capable of suspending the tongue away from the patient's throat during sleep; and
   securing the restrainer to the interior surface of the patient's mandible to suspend the tongue away from the patient's throat during sleep.

2. The method of claim 1 further comprising providing the restrainer in the form of a cylinder with a solid center section throughout the entire length of the cylinder.

3. The method of claim 2 further comprising providing the solid center section in the form of filaments and fibers.

4. The method of claim 1 wherein the lateral channel is formed by tongue tissue incision and dissection with a scalpel.

5. The method of claim 1 wherein the lateral channel is formed with an electrosurgical device.

6. The method of claim 1 wherein the lateral channel is formed by a needle passer that pulls the restrainer through the tongue tissue and tunnels through the tongue tissue.

7. The method of claim 1 further comprising providing the restrainer in the form of a planar sheet.

8. The method of claim 1 further comprising providing the restrainer in the form of at least one planar sheet with a solid portion positioned between two porous sections.

9. The method of claim 1 further comprising providing the restrainer in the form of at least two individual planar sections.

10. The method of claim 1 further comprising providing the restrainer in the form of two solid center end sections.

11. The method of claim 1 further comprising providing the restrainer in the form of a solid central section.

12. The method of claim 1, wherein the restrainer comprises an elastic material.

13. The method of claim 1 wherein the restrainer comprises pores that are sized and dimensioned to support growth of vascularized tissue within the restrainer.

* * * * *